(12) United States Patent
Cho et al.

(10) Patent No.: US 11,553,753 B2
(45) Date of Patent: Jan. 17, 2023

(54) PRESSURE SENSING INSOLE

(71) Applicant: LG INNOTEK CO., LTD., Seoul (KR)

(72) Inventors: Won Keun Cho, Seoul (KR); Bi Yi Kim, Seoul (KR); Jeong Han Kim, Seoul (KR); Yong Hwa Park, Seoul (KR); Hyun Gyu Park, Seoul (KR); Hyun Jin Jo, Seoul (KR); In Hee Cho, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 1093 days.

(21) Appl. No.: 15/774,523

(22) PCT Filed: Nov. 8, 2016

(86) PCT No.: PCT/KR2016/012819
§ 371 (c)(1),
(2) Date: May 8, 2018

(87) PCT Pub. No.: WO2017/082613
PCT Pub. Date: May 18, 2017

(65) Prior Publication Data
US 2020/0260815 A1    Aug. 20, 2020

(30) Foreign Application Priority Data

Nov. 9, 2015 (KR) .......... 10-2015-0156815

(51) Int. Cl.
*A43B 3/34* (2022.01)
*A61B 5/00* (2006.01)
(Continued)

(52) U.S. Cl.
CPC .............. *A43B 3/34* (2022.01); *A61B 5/6807* (2013.01); *A43B 17/006* (2013.01); *A43B 17/03* (2013.01);
(Continued)

(58) Field of Classification Search
CPC ......... A43B 3/34; A43B 17/006; A43B 17/03; A61B 5/6807; A61B 5/1036; A61B 2562/0247
See application file for complete search history.

(56) References Cited

U.S. PATENT DOCUMENTS 5,002,845 A * 3/1991 Shimura ................ G03G 5/047
430/58.65
6,195,921 B1 * 3/2001 Truong .................... A43B 3/00
36/137

FOREIGN PATENT DOCUMENTS

KR    10-2011-0124964    11/2011
KR    1020110124964    * 11/2011    ............. A43B 17/00
(Continued)

OTHER PUBLICATIONS

International Search Report (with English Translation) and Written Opinion dated Feb. 3, 2017 issued in Application No. PCT/KR2016/012819.

*Primary Examiner* — Doon Y Chow
*Assistant Examiner* — Dennis Chow
(74) *Attorney, Agent, or Firm* — Ked & Associates LLP

(57) ABSTRACT

A pressure sensing insole according to an embodiment of the present invention includes: a first electrode layer including a first conductive region; a first adhesive layer disposed on the first electrode layer and including an insulating region; an intermediate layer disposed on the first adhesive layer; a second adhesive layer disposed on the intermediate layer and including an insulating region; and a second electrode layer disposed on the second adhesive layer and including a second conductive region.

16 Claims, 5 Drawing Sheets

(51) Int. Cl.
*A43B 17/00* (2006.01)
*A43B 17/03* (2006.01)
*A61B 5/103* (2006.01)

(52) U.S. Cl.
CPC ..... *A61B 5/1036* (2013.01); *A61B 2562/0247* (2013.01)

(56) References Cited

FOREIGN PATENT DOCUMENTS

| | | |
|---|---|---|
| KR | 10-2014-0062541 | 5/2014 |
| KR | 10-2014-0128440 | 11/2014 |
| KR | 10-2015-0048019 | 5/2015 |
| KR | 10-1530225 | 6/2015 |
| WO | WO 2013/126751 | 8/2013 |

* cited by examiner

PRESSURE SENSING INSOLE

CROSS-REFERENCE TO RELATED PATENT APPLICATIONS

This application is a U.S. National Stage Application under 35 U.S.C. § 371 of PCT Application No. PCT/KR2016/012819, filed Nov. 8, 2016, which claims priority to Korean Patent Application No. 10-2015-0156815, filed Nov. 9, 2015, whose entire disclosures are hereby incorporated by reference.

TECHNICAL FIELD

The present invention relates to pressure sensing, and more particularly, to a pressure sensing insole.

BACKGROUND ART

Recently, with the development of electronic technology and information communication technology, a field of health care has been rapidly developing. That is, there has been a need for a health management system capable of measuring a body condition of a person using biometric information. For example, technology has been developed for detecting a wearer's health condition and walking posture by mounting a pressure sensor inside a shoe.

However, when pressure sensors are provided in a sole of a shoe or an insole, a plurality of pressure sensors are required, and additional space is required to insert the pressure sensors. In addition, since the pressure sensors are not flexible and stretchable, the pressure sensors are difficult to apply to a shoe having a curved shape, and a user is likely to feel a sensation of a foreign body.

DISCLOSURE

Technical Problem

The present invention is directed to providing a pressure sensing insole configured to sense pressure and a position according to weight applied thereto.

Technical Solution

One aspect of the present invention provides a pressure sensing insole including: a first electrode layer having a first conductive region; a first adhesive layer disposed on the first electrode layer and having an insulating region; an intermediate layer disposed on the first adhesive layer; a second adhesive layer disposed on the intermediate layer and having an insulating region; and a second electrode layer disposed on the second adhesive layer and having a second conductive region.

The conductive region of the second electrode layer may have at least one sensing region for sensing pressure and at least one connection region connected to the at least one sensing region.

The connection region of the second electrode layer may be disposed to correspond to at least one of the insulating region of the first adhesive layer and the insulating region of the second adhesive layer.

The insulating region of the first adhesive layer and the insulating region of the second adhesive layer may not be disposed below the sensing region of the second electrode layer.

The first adhesive layer and the second adhesive layer may not be disposed below the sensing region of the second electrode layer.

Each of the first adhesive layer and the second adhesive layer may have a hole formed in a portion corresponding to the sensing region of the second electrode layer.

The sensing region of the second electrode layer may directly come into contact with the intermediate layer when being pressed.

Each of the first conductive region and the second conductive region may be composed of a conductive fiber.

The conductive fiber may be a metal wire or a fiber coated with a metal film.

The intermediate layer may include an elastic body and a conductive composite dispersed in the elastic body.

The intermediate layer may include a plurality of stacked layers.

The pressure sensing insole may further include a connector connected to the at least one connection region and the first electrode layer and configured to receive an electric signal generated from the sensing region.

The pressure sensing insole may further include a signal processing module configured to process the electric signal received from the connector and a communication module configured to transmit the electric signal processed by the signal processing module to an external device.

Another aspect of the present invention provides a pressure sensing insole including: at least one sensing region; and a connection region connected to the sensing region, wherein each of the sensing region and the connection region includes a first conductive region composed of a conductive fiber, an intermediate layer disposed on the first conductive region, and a second conductive region composed of a conductive fiber and disposed on the intermediate layer, and the connection region further includes an insulating region formed between the first conductive region and the intermediate layer and between the intermediate layer and the second conductive region.

Advantageous Effects

A pressure sensing insole according to an exemplary embodiment of the present invention can precisely sense pressure according to weight applied thereto and may precisely sense a pressure distribution in a insole. In addition, when the pressure sensing insole according to the exemplary embodiment of the present invention is used, a separate space is not required to accommodate a sensor in a shoe. Furthermore, since the pressure sensing insole according to the exemplary embodiment of the present invention has high flexibility and stretchability, the pressure sensing insole can be applied to various types of shoes, and a user can comfortably wear the pressure sensing insole without feeling a sensation of a foreign body.

MODES OF THE INVENTION

Figure 1:
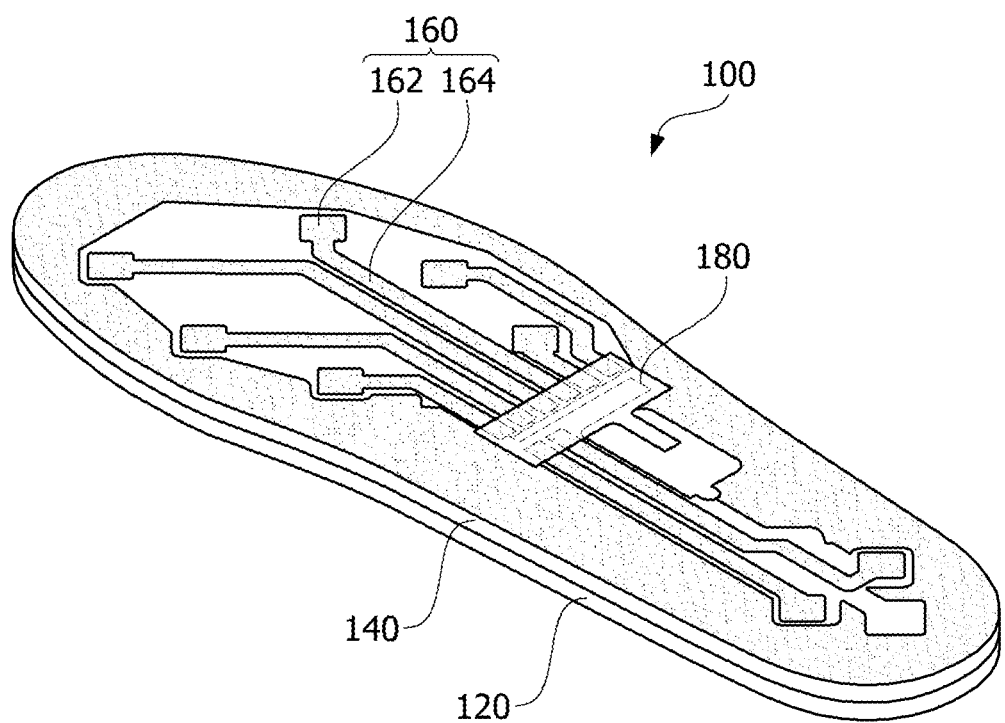
FIG. 1 is a perspective view illustrating a pressure sensing insole according to an exemplary embodiment of the present invention.

While the present invention is open to various modifications and alternative embodiments, specific embodiments thereof will be described and shown by way of example in the drawings. However, it should be understood that there is no intention to limit the present invention to the particular embodiments disclosed, and, on the contrary, the present invention is to cover all modifications, equivalents, and alternatives falling within the spirit and scope of the present invention.

It should be understood that, although terms including ordinal numbers such as "first," "second," and the like may be used herein to describe various elements, the elements are not limited by the terms. The terms are only used to distinguish one element from another. For example, a second element could be termed a first element without departing from the scope of the claims of the present invention, and similarly a first element could be also termed a second element. The term "and/or" includes any and all combinations of a plurality of associated listed items.

When one component is described as "connected to" or "accessing" another component, it may be connected to or access the corresponding component directly. However, other component(s) may exist in between. On the other hand, when one component is described as "directly connected to" or "directly accessing" another component, it should be understood that other component(s) may not exist in between.

The terminology used herein is for the purpose of describing particular embodiments only and is not intended to limit the present invention. A single form of expression is meant to include multiple elements unless otherwise stated. It should be understood that the terms "comprises," "comprising," "includes" and/or "including," when used herein, specify the presence of stated features, integers, steps, operations, elements, components and/or combinations thereof, but do not preclude the presence or addition of one or more other features, integers, steps, operations, elements, components and/or combinations thereof.

Unless defined otherwise, all the terms (including technical and scientific terms) used herein have the same meaning as commonly understood by one of ordinary skill in the art to which the present invention belongs. It will be further understood that the terms, such as those defined in commonly used dictionaries, should be interpreted as having meanings that are consistent with their meanings in the context of the relevant art, and will not be interpreted in an idealized or overly formal sense unless expressly defined otherwise herein Hereinafter, example embodiments are described with reference to the attached drawings, and same or corresponding elements regardless of drawing symbols will be given the same reference numbers, and redundant descriptions will be omitted.

Figure 2:
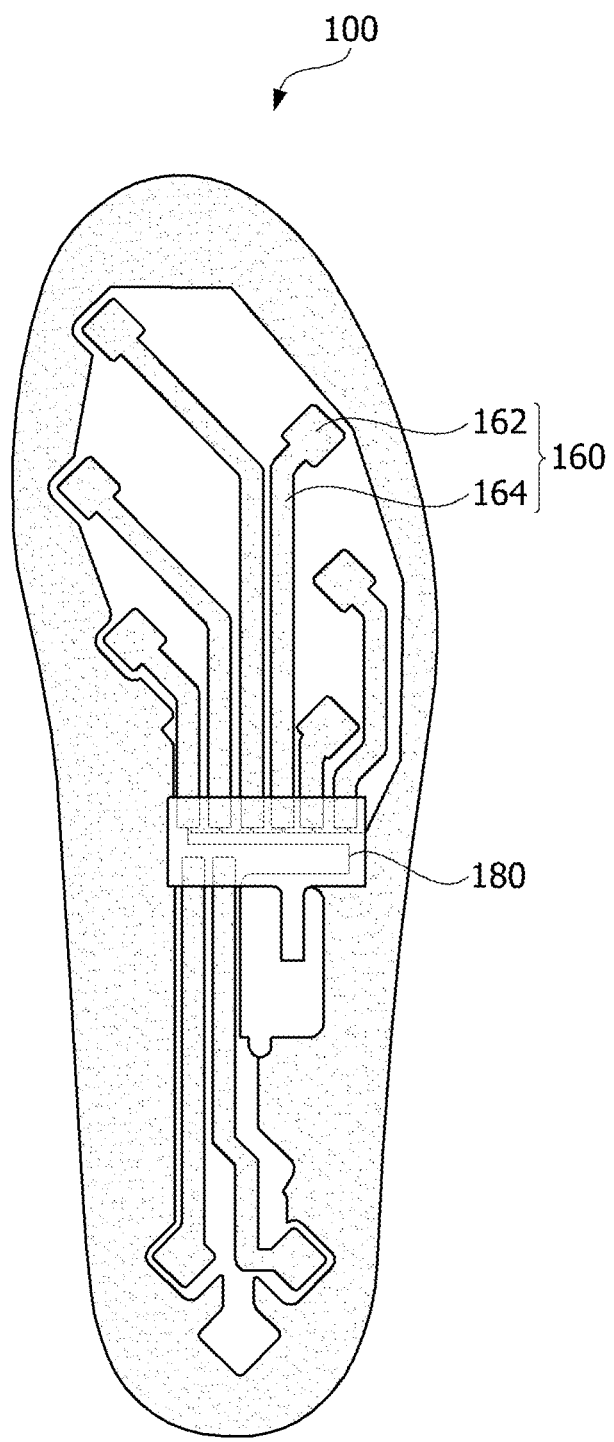
FIG. 2 is a top view illustrating the pressure sensing insole according to the exemplary embodiment of the present invention.
Figure 3:
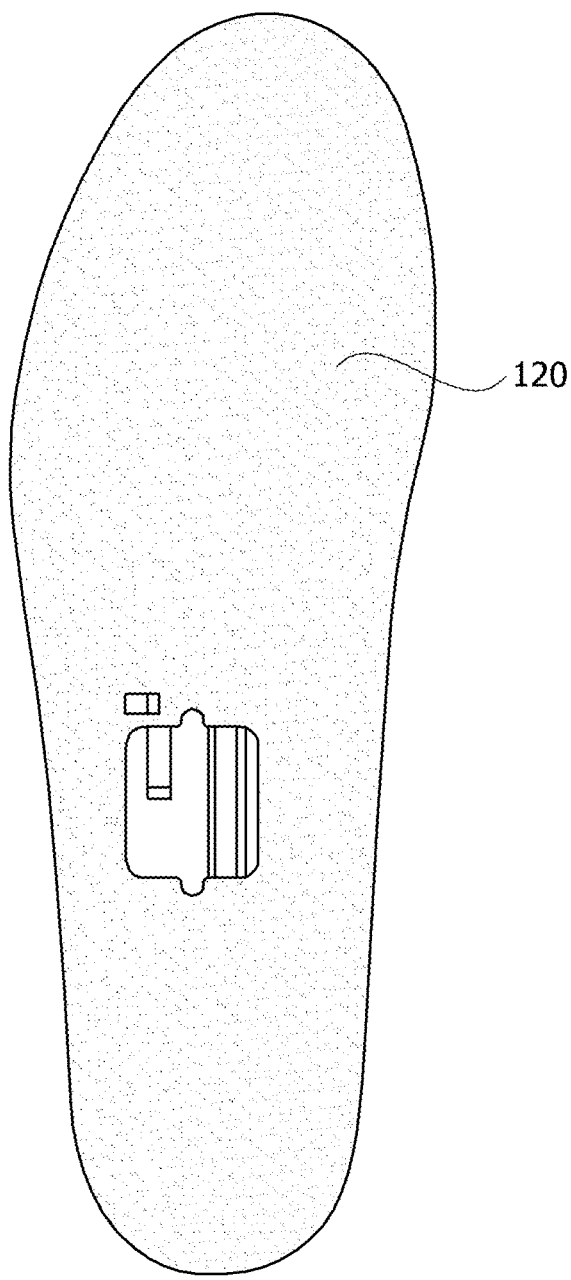
FIG. 3 is a bottom view illustrating the pressure sensing insole according to the exemplary embodiment of the present invention.
Figure 4:
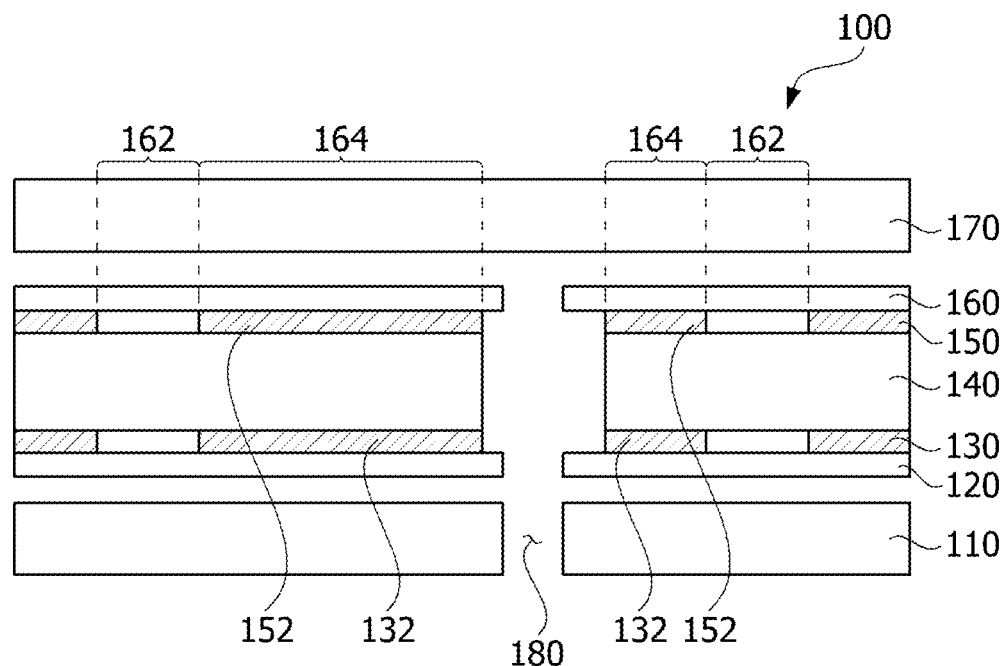
FIG. 4 is a cross-sectional view illustrating the pressure sensing insole according to the exemplary embodiment of the present invention.

FIG. 1 is a perspective view illustrating a pressure sensing insole according to an exemplary embodiment of the present invention. FIG. 2 is a top view illustrating the pressure sensing insole according to according to the exemplary embodiment of the present invention. FIG. 3 is a bottom view illustrating the pressure sensing insole according to the exemplary embodiment of the present invention. FIG. 4 is a cross-sectional view illustrating the pressure sensing insole according to the exemplary of the present invention.

Referring to FIGS. 1 to 4, the pressure sensing insole 100 includes a lower cover 110, a lower electrode layer 120, a lower adhesive layer 130, an intermediate layer 140, an upper adhesive layer 150, an upper electrode layer 160, and an upper cover 170.

The lower cover 110 and the upper cover 170 cover and protect the lower electrode layer 120 and the upper electrode layer 160, respectively.

Each of the lower electrode layer 120 and the upper electrode layer 160 is composed of a fabric and has a conductive region. In this case, the conductive region of each of the lower electrode layer 120 and the upper electrode layer 160 may be composed of a fabric which is woven with a conductive fiber. Here, the conductive fiber may be a metal wire or an ordinary fiber coated with a metal film. The conductive fiber may be an ordinary fiber in which metal particles are dispersed. When the conductive fiber is the metal wire, a diameter of the metal wire may be in a range of 10 μm to 500 μm. When the diameter of the metal wire is less than 10 μm, strength of the metal wire may be low. Thus, a fabric may be difficult to process. When the diameter of the metal wire is greater than 500 μm, strength of the metal wire may be high and then flexibility thereof may be low. Therefore, processing of the fabric may do damage to equipment, and a user may be likely to feel a sensation of a foreign body. In this case, the metal wire may be Cu, Ni, or a stainless steel alloy. For example, the stainless steel alloy may be at least one selected from a martensitic stainless steel alloy, a ferritic stainless steel alloy, an austenitic stainless steel alloy, a duplex stainless steel alloy, a precipitation hardening stainless steel alloy, and the like. When the metal wire is the stainless steel alloy, it is possible to increase corrosion resistance of the pressure sensing insole 100.

When the conductive fiber is the ordinary fiber coated with the metal film, the metal film may be formed by coating the ordinary fiber with metal particles through a plating process or a deposition process. In this case, the metal particles may be particles of Cu, Ni, or a stainless steel alloy, and a thickness of the metal film may be in a range of 1 μm to 50 μm. When the thickness of the metal film is less than 1 μm, conductivity is low such as to cause loss of a signal when the signal is transmitted. When the thickness of the metal film is greater than 50 μm, the metal film may be easily detached from a surface of a fiber.

Meanwhile, the conductive region of the upper electrode layer 160 may have at least one sensing region 162 for sensing pressure and at least one connection region 164 connected to the at least one sensing region 162.

The sensing region 162 may be disposed at each of points at which pressure is to be sensed. When pressure is applied to the sensing region 162, a thickness of the intermediate layer 140 having elasticity may be changed. Resistance of the intermediate layer 140 is changed, and as a result, electricity is conducted between the upper electrode layer 160 having the sensing region 162 and the lower electrode layer 120.

The connection region 164 and the lower electrode layer 120 are connected to a connector 180, and an electric signal generated from the sensing region 162 is transmitted to the connector 180. Here, the connector 180 may be implemented as a metal wiring on a flexible printed circuit board (FPCB), and may be disposed in a central region of the pressure sensing insole 100. Generally, the central region of the pressure sensing insole 100 is a region in which a concave portion of a sole is located. The central region of the pressure sensing insole 100 is not directly in contact with the sole. Therefore, durability of the connector 180 may be increased. Additionally, the connector 180 may be connected to a signal processing module (not shown) and a communication module (not shown). The signal processing module and the communication module may be detachably attached to a shoe or may be implemented in the form of a chip on an FPCB on which the connector 180 is disposed. The signal processing module may process an electric signal received through the connector 180, and the communication module may transmit an electric signal processed by the signal processing module to an external device (not shown). The external device may analyze a distribution of body pressure of a user applied to the pressure sensing insole 100 by using the electric signal received from the communication module. An analysis result may be applied in various applications.

Here, the connection region 164, the intermediate layer 140, and the lower electrode layer 120 may be insulated from one another. Accordingly, the pressure sensing insole 100 according to the exemplary embodiment of the present invention senses only pressure applied to the sensing region 162 and does not sense pressure applied to the connection region 164.

To this end, the lower adhesive layer 130 disposed between the lower electrode layer 120 and the intermediate layer 140, and the upper adhesive layer 150 disposed between the intermediate layer 140 and the upper electrode layer 160 may have insulating regions 132 and 152. The insulating region 132 of the lower adhesive layer 130 and the insulating region 152 of the upper adhesive layer 150 may be disposed below the connection region 164. An insulating region of the lower adhesive layer 130 and an insulating region of the upper adhesive layer 150 may not be disposed below the sensing region 162. In an example, the lower adhesive layer 130 and the upper adhesive layer 150 may have a structure in which an insulating adhesive is coated on both surfaces of a film. Portions of the lower adhesive layer 130 and the upper adhesive layer 150, which are disposed below the sensing region 162, may not be coated with an insulating adhesive. In another example, the lower adhesive layer 130 and the upper adhesive layer 150 may have a structure in which an adhesive is coated on both surfaces of a film. The lower adhesive layer 130 and the upper adhesive layer 150 may be additionally coated with an insulating material except for portions thereof which are disposed below the sensing region 162. In another example, the lower adhesive layer 130 and the upper adhesive layer 150 may have a structure in which an adhesive including an insulating material is coated on both surfaces of a film. Portions of the lower adhesive layer 130 and the upper adhesive layer 150, which are disposed below the sensing region 162, may be punched. That is, each of the lower adhesive layer 130 and the upper adhesive layer 150 may have a hole formed in a portion thereof corresponding to the sensing region 162. Thus, since the lower adhesive layer 130 and the upper adhesive layer 150 are not disposed below the sensing region 162, the sensing region 162 and also the lower electrode layer 120 disposed below the sensing region 162 may directly come into contact with the intermediate layer 140 when being pressed.

On the other hand, the intermediate layer 140 may include an elastic body and a conductive composite dispersed in the elastic body. Here, the elastic body may be a synthetic fiber, a natural fiber, an elastomer, rubber, urethane, or the like, the synthetic fiber including one selected from the group consisting of a fiber material, polyurethane, nylon, polyethylene terephthalate, and polyester, which have a random fiber arrangement of foam, a non-woven fabric, a nanoweb, or the like. Accordingly, the intermediate layer 140 has fine pores and elasticity. In this case, a thickness of the intermediate layer 140 may be in a range of 1 mm to 4 mm. When the thickness of the intermediate layer 140 is less than 1 mm, it may be difficult for the intermediate layer 140 to maintain an insulating function in a normal state, i.e., in a state in which an external force is not applied. When an external force is applied, a change in the thickness may be small, and thus, a change in resistance may be small. Accordingly, pressure sensing efficiency may be lowered. When the thickness of the intermediate layer 140 is greater than 4 mm, the intermediate layer 140 may be difficult to apply in a shoe.

On the other hand, the conductive composite included in the intermediate layer 140 may be coated on a surface of a fiber constituting an elastic body or may be dispersed in the elastic body.

Accordingly, the intermediate layer 140 has an insulating characteristic, i.e., a resistance of 1 kΩ or more. However, when a physical change occurs around the intermediate layer 140, that is, when pressure is applied to the sensing region 162, the thickness of intermediate layer 140 disposed below the sensing region 162 is reduced, so that resistance of the intermediate layer 140 is changed.

To this end, the conductive composite may include a conductive polymer and a conductive powder. An amount of the conductive composite may be included in a range of 1 wt % to 10 wt % of the elastic body. When the amount of the conductive composite is greater than 10 wt % of the elastic body, it is difficult to ensure an insulating characteristic in a state in which pressure is not applied. In this case, the conductive polymer may include polyaniline or polypyrrole. The conductive powder may include one selected from the group consisting of Au, Ag, Cu, Ni, a carbon nanotube (CNT), graphene, and a ceramic filler.

In this case, the conductive powder may have a spherical shape, a spicule shape, or a plate shape and a diameter of the conductive powder may be in a range of 10 nm to 500 μm. When the diameter of the conductive powder is less than 10 nm, the conductive powder is difficult to disperse in the conductive polymer. Interfacial resistance between particles is high, and total resistance of the intermediate layer 140 is decreased. When the diameter of the conductive powder is greater than 500 μm, a surface of the intermediate layer 140 may not be smooth, frictional force may increase, and thus, the intermediate layer 140 may be difficult to process.

On the other hand, the intermediate layer 140 may have a structure in which a plurality of layers are stacked.

Figure 5:
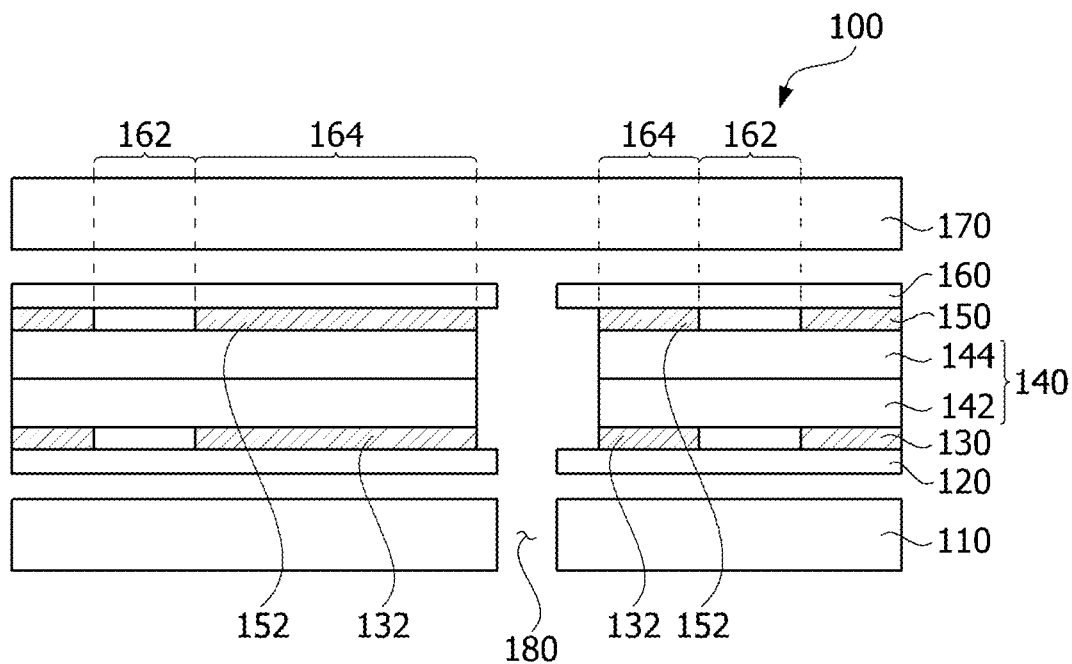
FIG. 5 is a cross-sectional view illustrating a pressure sensing insole according to another exemplary embodiment of the present invention.

FIG. 5 is a cross-sectional view illustrating a pressure sensing insole according to another exemplary embodiment of the present invention. Redundant descriptions of the same contents in FIGS. 1 to 4 will be omitted.

Referring to FIG. 5, the pressure sensing insole 100 includes a lower cover 110, a lower electrode layer 120, a lower adhesive layer 130, an intermediate layer 140, an upper adhesive layer 150, an upper electrode layer 160, and an upper cover 170.

Here, the intermediate layer 140 may include a first intermediate layer 142 and a second intermediate layer 144 which are vertically stacked. In this case, the first intermediate layer 142 and the second intermediate layer 144 may not be attached to each other and may simply be stacked. Alternatively, the first intermediate layer 142 and the second intermediate layer 144 may not be completely attached to each other and may be partially attached to each other. For example, the first intermediate layer 142 and the second intermediate layer 144 may be attached along edges thereof or be attached to each other so as to correspond to a region of the upper electrode layer 160 except for a conductive region of the upper electrode layer 160 or to correspond to a conductive region of the upper electrode layer 160 except for a sensing region of the upper electrode layer 160. Accordingly, an air layer may be present between the first intermediate layer 142 and the second intermediate layer 144. It has been described that the intermediate layer 140 includes the first intermediate layer 142 and the second intermediate layer 144. However, the present invention is not limited thereto, and the intermediate layer 140 may include two or more intermediate layers stacked.

Each of the first intermediate layer 142 and the second intermediate layer 144 may include an elastic body and a conductive composite dispersed in the elastic body. Here, the elastic body may be a synthetic fiber, a natural fiber, an elastomer, rubber, urethane, or the like, the synthetic fiber including one selected from the group consisting of a fiber material, polyurethane, nylon, polyethylene terephthalate, and polyester, which have a random fiber arrangement of foam, a non-woven fabric, a nanoweb, or the like. The conductive composite may include a conductive polymer and a conductive powder. In this case, the conductive polymer may include polyaniline or polypyrrole. The conductive powder may include one selected from the group consisting of Au, Ag, Cu, Ni, carbon nanotube (CNT), graphene, and a ceramic filler.

Figure 6:
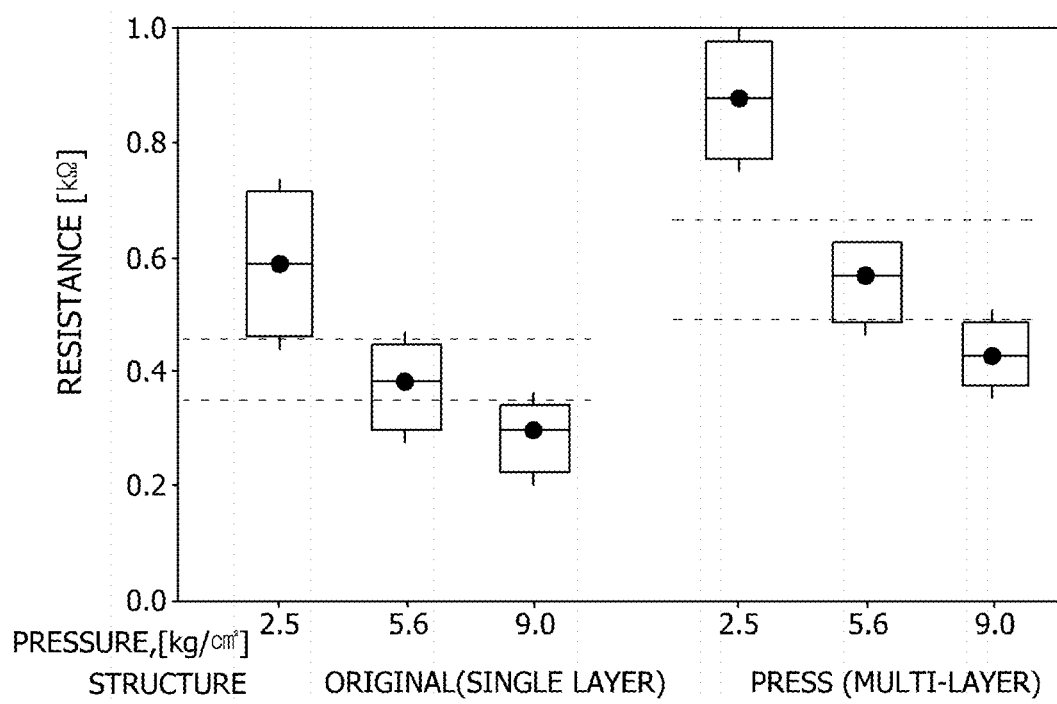
FIG. 6 is a diagram illustrating a resolution comparison between a case in which an intermediate layer is formed in a single layer structure and a case in which an intermediate layer is formed in a multi-layer structure.

As described above, when the intermediate layer 140 is formed in a plurality of layers, resolution of the intermediate layer 140 may be increased. As a result, applied pressure can be more precisely sensed. FIG. 6 is a diagram illustrating a resolution comparison between a case in which an intermediate layer is formed in a single layer structure and a case in which an intermediate layer is formed in a multi-layer structure.

Here, resistance values were measured after applying pressures of 2.5 kg/cm$^2$, 5.6 kg/cm$^2$, and 9.0 kg/cm$^2$ in the same conditions such as the same material, the same density, and the same thickness with respect to the intermediate layer formed in the single layer structure and the intermediate layer formed in the multi-layer structure. Resistance values of four samples were measured in each condition, and maximum and minimum values of the resistance values measured in each condition were shown.

Referring to FIG. 6, in the case of the intermediate layer formed in the single layer structure, it can be seen that when a pressure of 5.6 kg/cm$^2$ is applied and when a pressure of 9.0 kg/cm$^2$ is applied, measured resistance values are partially overlapping. Therefore, it may be difficult to accurately sense applied pressure only by a resistance value.

On the contrary, in the case of the intermediate layer formed in the multi-layer structure, when different pressures are applied, measured values are not overlapping.

In addition, a difference between resistance values measured when a pressure of 2.5 kg/cm$^2$ is applied and when a pressure of 9.0 kg/cm$^2$ is applied in the case of the intermediate layer formed in the multi-layer structure is greater than a difference between resistance values measured when a pressure of 2.5 kg/cm$^2$ is applied and when a pressure of 9.0 kg/cm$^2$ is applied in the case of the intermediate layer formed in the single layer structure.

From this, it can be seen that the intermediate layer formed in the multi-layer structure has excellent piezoresistive resolution for each pressure section, compared to that of the intermediate layer formed in the single layer structure.

In the present specification, the lower electrode layer, the lower adhesive layer, the intermediate layer, the upper adhesive layer, and the upper electrode layer have been described as an example for being included in an insole. However, the present invention is not limited thereto, and the lower electrode layer, the lower adhesive layer, the intermediate layer, the upper adhesive layer, and the upper electrode layer according to the exemplary embodiment of the present invention may be included in a sole of a shoe.

As described above, exemplary embodiments of the present invention have been described with reference to the accompanying drawings. However, the present invention is not limited to the above-described exemplary embodiments. It may be apparent to one who has ordinary skill in the art that there may be many modifications and variations within the technical spirit of the present invention.

REFERENCE NUMERALS

100: PRESSURE SENSING INSOLE
110: LOWER COVER
120: LOWER ELECTRODE LAYER
130: LOWER ADHESIVE LAYER
140: INTERMEDIATE LAYER
150: UPPER ADHESIVE LAYER
160: UPPER ELECTRODE LAYER
170: UPPER COVER
162: SENSING REGION
164: CONNECTION REGION

The invention claimed is:
1. A pressure sensing insole comprising:
a first electrode layer having a first conductive region;
a first adhesive layer disposed on the first electrode layer and having an insulating region;
an intermediate layer disposed on the first adhesive layer, wherein the intermediate layer includes a plurality of stacked layers;
a second adhesive layer disposed on the intermediate layer and having an insulating region; and
a second electrode layer disposed on the second adhesive layer and having a second conductive region, wherein the conductive region of the second electrode layer has at least one sensing region for sensing pressure and at least one connection region connected to the at least one sensing region,
wherein the intermediate layer includes an elastic body and a conductive composite dispersed in the elastic body,
wherein the sensing region of the second electrode layer directly comes into contact with one of the stacked layers of the intermediate layer when being pressed.
2. The pressure sensing insole of claim 1, wherein the connection region of the second electrode layer is disposed to correspond to at least one of the insulating region of the first adhesive layer and the insulating region of the second adhesive layer.
3. The pressure sensing insole of claim 2, wherein the insulating region of the first adhesive layer and the insulating region of the second adhesive layer are not disposed below the sensing region of the second electrode layer.

4. The pressure sensing insole of claim 3, wherein the first adhesive layer and the second adhesive layer are not disposed below the sensing region of the second electrode layer.

5. The pressure sensing insole of claim 4, wherein each of the first adhesive layer and the second adhesive layer has a hole formed in a portion corresponding to the sensing region of the second electrode layer.

6. The pressure sensing insole of claim 1, wherein each of the first conductive region and the second conductive region is composed of a conductive fiber.

7. The pressure sensing insole of claim 6, wherein the conductive fiber is a metal wire or a fiber coated with a metal film.

8. The pressure sensing insole of claim 1, wherein the conductive composite is included in a range of 1 wt % to 10 wt % of the elastic body.

9. The pressure sensing insole of claim 1, further comprising a connector connected to the at least one connection region and the first electrode layer and configured to receive an electric signal generated from the sensing region.

10. The pressure sensing insole of claim 9, further comprising a signal processing module configured to process the electric signal received from the connector and a communication module configured to transmit the electric signal processed by the signal processing module to an external device.

11. A pressure sensing insole comprising:
at least one sensing region; and
a connection region connected to the sensing region,
wherein each of the sensing region and the connection region includes a first conductive region composed of a conductive fiber, an intermediate layer disposed on the first conductive region, and a second conductive region composed of a conductive fiber and disposed on the intermediate layer, and
the connection region further includes an insulating region formed between the first conductive region and the intermediate layer and between the intermediate layer and the second conductive region,
wherein the intermediate layer includes an elastic body and a conductive composite dispersed in the elastic body,
wherein the intermediate layer includes a plurality of stacked layers,
wherein the sensing region directly comes into contact with one of the stacked layers of the intermediate layer when being pressed.

12. The pressure sensing insole of claim 11, wherein the conductive fiber is a metal wire or a fiber coated with a metal film.

13. The pressure sensing insole of claim 11, wherein the conductive composite is included in a range of 1 wt % to 10 wt % of the elastic body.

14. The pressure sensing insole of claim 8, wherein the conductive composite includes a conductive polymer and a conductive powder.

15. The pressure sensing insole of claim 14, wherein the conductive polymer includes at least one of polyaniline or polypyrrole, and the conductive powder includes at least one selected from a group consisting of Au, Ag, Cu, Ni, a carbon nanotube (CNT), graphene, and a ceramic filler.

16. The pressure sensing insole of claim 1, wherein the intermediate layer includes a first intermediate layer and a second intermediate layer stacked on the first intermediate layer, and an air layer is present in at least a part of a region between the first intermediate layer and the second intermediate layer.

* * * * *